United States Patent
Murthy

(10) Patent No.: US 9,157,890 B2
(45) Date of Patent: Oct. 13, 2015

(54) EXCHANGE MEMBRANE UNIT AND SYSTEM INCLUDING EXCHANGE MEMBRANE UNIT

(71) Applicant: ATONARP INC., Hachioji-shi (JP)

(72) Inventor: Prakash Sreedhar Murthy, Tsukuba (JP)

(73) Assignee: ATONARP INC., Hachioji-Shi, Tokyo (JP)

( * ) Notice: Subject to any disclaimer, the term of this patent is extended or adjusted under 35 U.S.C. 154(b) by 0 days.

(21) Appl. No.: 14/402,755

(22) PCT Filed: Sep. 4, 2013

(86) PCT No.: PCT/JP2013/005230
§ 371 (c)(1),
(2) Date: Nov. 21, 2014

(87) PCT Pub. No.: WO2014/038194
PCT Pub. Date: Mar. 13, 2014

(65) Prior Publication Data
US 2015/0177190 A1    Jun. 25, 2015

(30) Foreign Application Priority Data

Sep. 4, 2012    (JP) ................. 2012-194089

(51) Int. Cl.
*B01D 53/22* (2006.01)
*G01N 27/68* (2006.01)
(Continued)

(52) U.S. Cl.
CPC ............ *G01N 27/68* (2013.01); *B01D 19/0031* (2013.01); *B01D 53/32* (2013.01); *B01D 2259/818* (2013.01); *G01N 27/40* (2013.01)

(58) Field of Classification Search
CPC ............... B01D 19/0031; B01D 53/32; B01D 2259/818; G01N 27/40; G01N 27/68
See application file for complete search history.

(56) References Cited

U.S. PATENT DOCUMENTS 4,023,398 A * 5/1977 French et al. .................. 73/23.2
4,849,628 A * 7/1989 McLuckey et al. ........... 250/282
(Continued)

FOREIGN PATENT DOCUMENTS

JP        4-319244 A    11/1992
JP        2004-77361 A   3/2004
WO    WO 2012/056709 A1   5/2012

OTHER PUBLICATIONS

Youngzhai et al. Membrane-Extraction Ion Mobility Spectrometry for in Situ Detection of Chlorinated Hydrocarbons in Water Anal. Chem. 2010, 82, 4089-4096.*
(Continued)

*Primary Examiner* — Jason M Greene
*Assistant Examiner* — Anthony Shumate
(74) *Attorney, Agent, or Firm* — Buchanan Ingersoll & Rooney PC

(57) ABSTRACT

An exchange membrane unit includes a first separation membrane, a first space that is connected to a second space via the first separation membrane, a first path that supplies a first fluid (carrier gas) to the first space and supplies chemical substances, which have passed through the first separation membrane from the second space into the first space and diffused, to an ion detector using the first fluid discharged from the first space, and a first ionizing unit provided in the first space. It is possible to provide a preprocessing system that produces little pollution and enables an ion detector to operate with high sensitivity. The present invention can be applied to FAIMS.

8 Claims, 3 Drawing Sheets

(51) Int. Cl.
    *B01D 19/00*      (2006.01)
    *B01D 53/32*      (2006.01)
    *G01N 27/40*      (2006.01)

(56) References Cited

U.S. PATENT DOCUMENTS

| | | | | |
|---|---|---|---|---|
| 5,976,223 | A * | 11/1999 | Prasad et al. | 95/54 |
| 6,149,714 | A * | 11/2000 | Kobayashi | 95/54 |
| 6,620,320 | B1 * | 9/2003 | Hying et al. | 210/500.25 |
| 6,768,109 | B1 * | 7/2004 | Brokaw et al. | 250/298 |
| 7,416,803 | B2 * | 8/2008 | Haile et al. | 429/491 |
| 8,093,552 | B2 * | 1/2012 | Macknis | 250/286 |
| 8,742,363 | B2 * | 6/2014 | Munchmeyer et al. | 250/423 P |
| 8,866,075 | B2 * | 10/2014 | Sato et al. | 250/288 |
| 8,906,137 | B2 * | 12/2014 | Hilbig et al. | 95/54 |
| 2003/0201387 | A1 * | 10/2003 | Hartley et al. | 250/281 |
| 2007/0009778 | A1 * | 1/2007 | Chisholm et al. | 429/33 |
| 2008/0283411 | A1 * | 11/2008 | Eastman et al. | 205/343 |
| 2011/0284394 | A1 * | 11/2011 | Masel et al. | 205/783 |
| 2013/0052111 | A1 * | 2/2013 | Chew | 423/223 |
| 2014/0131197 | A1 * | 5/2014 | Suzuka et al. | 204/283 |
| 2014/0154811 | A1 * | 6/2014 | Sjong et al. | 436/72 |
| 2014/0318969 | A1 * | 10/2014 | Medoff et al. | 204/540 |

OTHER PUBLICATIONS

International Search Report (PCT/ISA/210) mailed on Oct. 29, 2013, by the Japanese Patent Office as the International Searching Authority for International Application No. PCT/JP2013/005230, 4 pg with translation.

Written Opinion (PCT/ISA/237) mailed on Oct. 29, 2013, by the Japanese Patent Office as the International Searching Authority for International Application No. PCT/JP2013/005230, 3pg.

Notification of Transmittal of Translation of the International Preliminary Report on Patentability (Forms PCT/IB/338 and PCT/IB/373) and the Written Opinion of the International Searching Authority (Form PCT/ISA/237) issued on Mar. 10, 2015, in the corresponding International Application No. PCT/JP2013/005230. (5 pages).

* cited by examiner

EXCHANGE MEMBRANE UNIT AND SYSTEM INCLUDING EXCHANGE MEMBRANE UNIT

TECHNICAL FIELD

The present invention relates to an exchange membrane unit used for preprocessing when detecting ions.

BACKGROUND ART

PCT publication WO2012/056709 discloses a system with a unit for analyzing samples that was proposed by the present applicant. The unit for analyzing includes: a functional unit that detects peaks that are present in a two-dimensional representation of data included in measurement data obtained by feeding a sample to an ion mobility sensor for measuring the ionic strength of ionized chemical substances that pass through an electric field controlled by at least two parameters, the two-dimensional representation indicating the ionic strength when a first parameter has been changed and the other parameter is fixed; a functional unit that classifies the peaks detected on the basis of the continuity between and the birth and death of the detected peaks and the other peaks that are present in the two-dimensional representation; and a functional unit that estimates the chemical substances contained in the sample on the basis of the classified peaks.

DISCLOSURE OF THE INVENTION

Extraction of volatile components from a solid, liquid, or gas sample using various types of fiber or membranes is carried out as preprocessing for gas chromatography. However, when trying to detect an extremely small amount of the components, for example, when carrying out detection with a concentration at ppb or ppt level using an ion mobility sensor, dirt (contamination) adhering to the fibers or membrane obstructs the measurement.

A first aspect of the present invention is an exchange membrane unit including: a first separation membrane; a first space that is connected to a second space via the first separation membrane; a first path that supplies a first fluid to the first space and supplies chemical substances, which have passed through the first separation membrane from the second space into the first space and diffused, to an ion detector using the first fluid discharged from the first space; and a first ionizing unit provided in the first space. The first fluid is typically a gas, which is a carrier gas.

By installing an ionizing unit in the first space, it is possible to ionize components (chemical substances, molecules) that have passed through the first separation membrane and reached the first space. In this unit, it is possible to pass specified components and/or to exclude specified components using the first separation membrane and also possible to suppress adhesion of components that have passed through the first separation membrane to the surface of the first separation membrane, the inside of the housing that defines the first space, and also the first piping. Accordingly, it is possible to prevent a phenomenon called pollution from occurring. A typical example of the first separation membrane is a gas permeation membrane (separating permeable membrane) capable of selectively not passing (separating) water (moisture, steam).

The components that have passed through the first separation membrane are not originally pollutants (contaminants), and are chemical substances to be detected that are included in a second fluid (sample fluid) supplied to or present in the second space. The exchange membrane unit ionizes the chemical substances, which have passed through the first separation membrane and diffused from the second space into the first space, using the ionizing unit installed in the first space. Accordingly, it is possible to prevent the chemical substances to be detected from becoming polluting substances and, by ionizing the chemical substances to be detected, to also improve the detection sensitivity for chemical substances at the ion detector.

Such pollutants can be understood as a time delay in transmission due to adhesion and the like of the chemical substances. This exchange membrane unit suppresses the generation of a time delay in the transmission of chemical substances by quickly ionizing chemical substances that have passed through the first separation membrane. Therefore, in addition to the function of separating gases, the exchange membrane unit is capable of suppressing the generation of pollution and is capable of suppressing time delays for the chemical substances that reach the ion detector. It is possible to ensure (increase) the amount of chemical substances that reach the ion detector installed downstream of the exchange membrane unit and to improve the detection sensitivity.

The first ionizing unit may be an indirect ionizing unit or may be a direct ionizing unit. A unit that uses $Ni_{63}$ and a unit that uses corona discharge can be given as examples of indirect ionizing units. A UV ionizing unit including an ultraviolet light source such as an ultraviolet light-emitting diode (UV-LED) or an ultraviolet lamp (UV-Low pressure lamp) can be given as an example of a direct ionizing unit. A favorable example of the first ionizing unit is a unit that generates atmospheric pressure plasma using corona discharge, RF discharge, or the like.

The first space is an almost closed space but the first fluid can communicate with and the second space may be open or may be closed. The second space may have a second path that supplies and discharges a second fluid. In this case, it is desirable for the exchange membrane unit to include a second ionizing unit provided in the second space. The second space is an almost closed space but the second fluid can communicate with and it is possible to prevent pollution of the second space.

The exchange membrane unit may further include a second separation membrane that connects the second space and the third space and third piping that supplies and discharges a third fluid to and from the third space. By using a dried gas composed of specified components, for example an inert gas such as nitrogen, as the second fluid that flows in the second space sandwiched between the first separation membrane and the second separation membrane, it is possible to remove water and supply a sample with lower humidity to the ion detector. It is possible to prevent water from obstructing measurement and detection at the ion detector.

It is desirable for the exchange membrane unit to include a thermoelectric conversion element (Peltier element) that heats and cools the first separation membrane. By setting the first separation membrane at low temperature, it is possible to suppress diffusion of chemical substances (molecules) into the first space and to accumulate the chemical substances at the first separation membrane. After this, by setting the first separation membrane at high temperature, it is possible to promote discharging of the molecules that have been accumulated at the first separation membrane. Accordingly, it is possible to use the exchange membrane unit as a simple buffer and to raise the concentration of chemical substances that pass through the exchange membrane unit.

Another aspect of the present invention is a system including the exchange membrane unit described above and the ion detector. Although a typical example of such system is a measurement apparatus, the system may be a system that includes a variety of applications such as using detection results for chemical substances as information for the provision of content and/or as information for detecting danger, or may be a system that is compatible with various applications. Although the ion detector may be a mass spectrometer, gas chromatography, or the like, an ion mobility sensor that is capable of detecting ionized molecules in a gas in real time is favorable.

DETAIL DESCRIPTION

Figure 1:
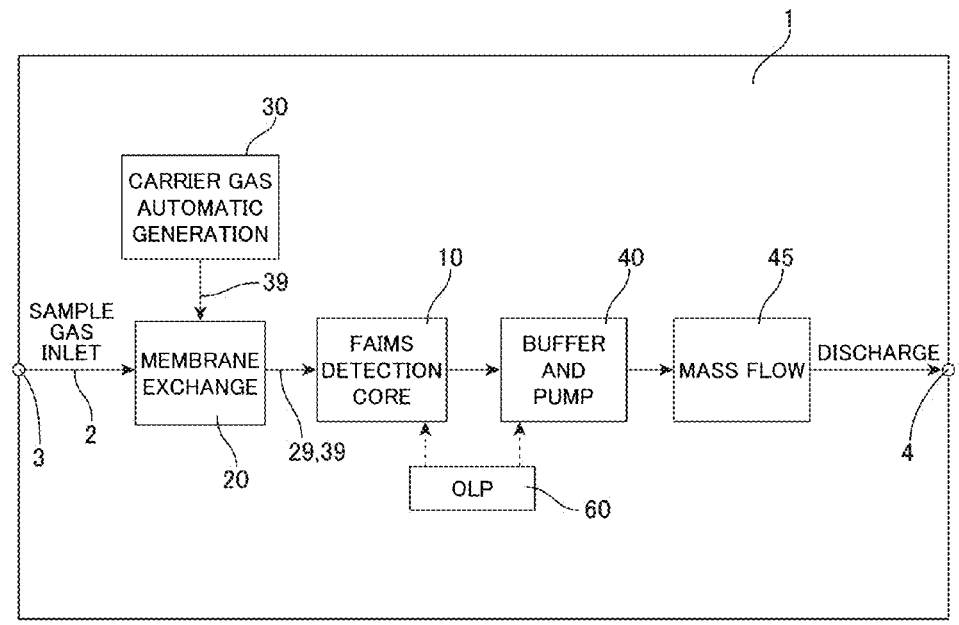
FIG. 1 is a block diagram showing the overall configuration of a measurement apparatus.

FIG. 1 shows an overview of an apparatus that detects and measures components included in a sample fluid. This measurement apparatus (measurement system) 1 includes an input (inlet) port 3 for a sample fluid 2 and a discharge port 4 that discharges gas that has been measured. The measurement apparatus 1 includes an exchange membrane unit (preprocessing unit) 20 that extracts chemical substances, for example, volatile components to be measured from the sample fluid 2, an ion mobility sensor 10 that is an ion detector that detects the extracted components 29, a gas generator 30 that generates a carrier gas 39 for carrying the extracted components 29 to the ion mobility sensor 10, a pump unit 40 that draws the carrier gas 39 to the ion mobility sensor 10, and a mass flow control apparatus (mass flow controller) 45 that carries out flow control of the carrier gas 39.

One example of the ion mobility sensor 10 is a FAIMS (Field Asymmetric waveform Ion Mobility Spectrometry, or DIMS (Differential Ion Mobility Spectrometry)). With FAIMS (FAIMS technology), the chemical substance to be measured is a compound, composition, molecule, or other product that can be ionized by an ionization unit disposed upstream of the FAIMS 10. FAIMS uses a property whereby ion mobility is unique for each chemical substance and applies a differential voltage (DV, Dispersion Voltage, Vd voltage, field voltage, AC voltage, hereinafter "Vf") and a compensation voltage (CV, compensation voltage, DC voltage, hereinafter "Vc") while causing ionized molecules (chemical substances) that are to be measured to move in an electric field. By appropriately controlling the values of Vf and Vc, an ionized chemical substance that is the detection target will reach a detection electrode and be detected as a current value.

The measurement apparatus 1 further includes a device (olfaction processor, OLP) 60 equipped with a function for controlling the amount of flow passing the ion mobility sensor 10 and analyzing measurement data obtained from the ion mobility sensor 10. The OLP 60 may be realized by general-purpose hardware resources (including a CPU and memory) of a personal computer or the like or may be provided as a single integrated device (semiconductor chip, ASIC, LSI) or a plurality of integrated chips (a chip set). The OLP 60 includes a function for controlling the measurement conditions or the environment of the FAIMS 10, a function of analyzing (interpreting) the measurement results according to measurement conditions or the environment, or the like, and is disclosed in detail in an application (PCT publication WO2012/056709) submitted by the present applicant.

Figure 2:
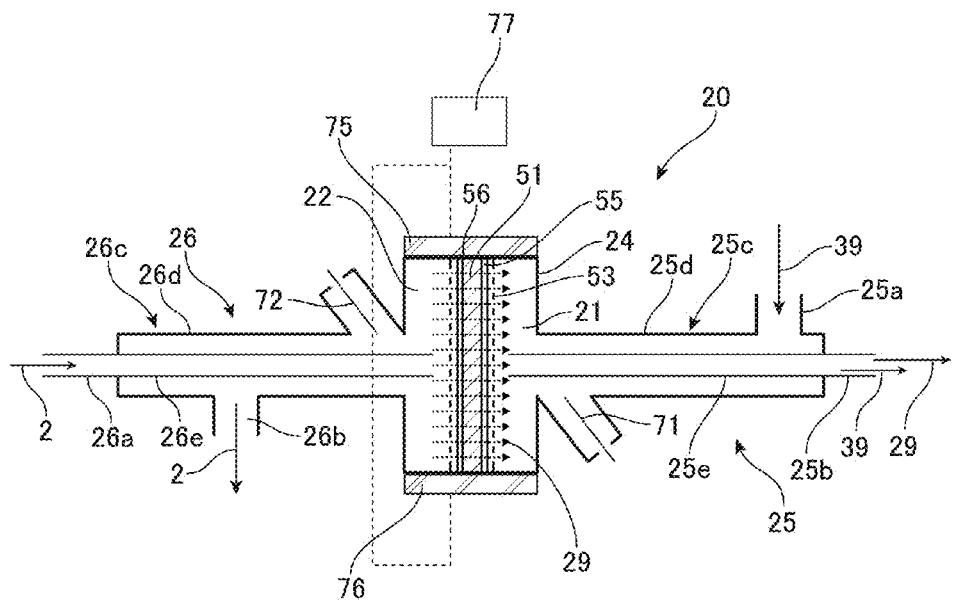
FIG. 2 is a block diagram showing an overview of an exchange membrane unit.

FIG. 2 shows the overall configuration of the exchange membrane unit 20. The exchange membrane unit (membrane unit for exchanging, membrane exchange unit) 20 includes a cylindrical housing 24 and a first separation membrane 51 held in the housing 24, so that the inside of the housing 24 is separated (divided) by the first separation membrane 51 into a first space (first room, first chamber) 21 and a second space (second room, second chamber) 22. Accordingly, the first space 21 is connected via the first separation membrane 51 to the second space 22. The exchange membrane unit 20 further includes first piping 25 that supplies and discharges a first fluid (carrier gas) 39 into and from the first space 21 and second piping 26 that supplies and discharges a second fluid (sample gas) 2 into and from the second space 22.

The first piping system 25 supplies the carrier gas 39 that is the first fluid, to the first space 21 and functions as a first path that supplies chemical substances, which have passed through the first separation membrane 51 from the second space 22 into the first space 21 and diffused, to the ion mobility sensor 10 that is the ion detector by way of the carrier gas 39 discharged from the first space 21. The first path may be flow paths formed by undulations or the like in a substrate. The first piping 25 includes an input (inlet) port 25a for the carrier gas 39 and an output (outlet) port 25b for the carrier gas 39, with the output port 25b being connected to the ion mobility sensor 10.

In more detail, the first piping system 25 includes a double-walled pipe 25c with the input port 25a provided on an outer pipe 25d and the output port 25b provided on an inner pipe 25e. The outer pipe 25d is arranged (constructed) so as to supply the carrier gas 39 to the entire first space 21 or from an outer side of the first space 21 and the inner pipe 25e is arranged (constructed) so as to be capable of discharging the carrier gas 39 from the vicinity of the first separation membrane 51. Accordingly, the first piping system 25 is capable of outputting the carrier gas 39 that includes a larger amount of the target chemical substances 29 that have passed through the first separation membrane 51 from the output port 25b.

The second piping system 26 fulfills a function as a second path that supplies and discharges a sample gas 2 that is the second fluid into and from the second space 22. The second path may be flow paths formed by undulations or the like in a substrate. The second piping 26 includes an input port 26a for the sample gas 2 and a discharge (output) port 26b for the sample gas 2, with the input port 26a being joined to the input port 3 of the measurement apparatus 1.

In more detail, the second piping system 26 includes a double-walled pipe 26c with the input port (sample input) 26a provided on an inner pipe 26e and the output port (sample output) 26b provided on an outer pipe 26d. The inner pipe 25e is constructed so as to guide the sample gas 2 to the vicinity of the first separation membrane 51. The outer pipe 26d is constructed so as to discharge the sample gas 2 from the periphery or the outside of the second space 22.

Accordingly, the second piping system 26 is capable of guiding the sample gas 2 to the vicinity of the first separation membrane 51 and discharging gas including a large amount of components that have not passed through the first separation membrane 51, that is, components that have been separated or excluded by the first separation membrane 51.

Using the exchange membrane unit 20, the chemical substances (target substances) 29 that have diffused into the first space 21 from the second space 22 via the separation membrane 51 are supplied by the carrier gas 39 that is the first fluid, to the ion mobility sensor 10.

A typical example of the first separation membrane 51 is a gas permeation membrane that includes PDMS (polydimethylsiloxane), hybrid silica and the like. A membrane of PDMS or hybrid silica is especially suited to removing water (steam, moisture) from the sample gas 2. PDMS is a polymer membrane material where the distance between polymer chains is large and which has a high gas permeability coefficient. Accordingly, PDMS functions as a porous membrane with an extremely fine pore diameter and according to reports is hydrophobic, has a high affinity for organic liquids, and has excellent selective permeability. The PDMS in the present specification includes modified PDMS prepared by a crosslinking reaction between conventional PDMS and polymers such as various di-vinyl monomers, and a composite membrane composed of PDMS and other materials.

The hybrid silica is a microporous organic-inorganic hybrid membrane that has an average pore diameter of 0.1 to 0.6 nm and is based on silica that is hydrothermally stable up to at least 200° C. in several types of medium, and can be manufactured using a sol-gel process on short-chain, cross-linked silane. It has been reported that hybrid silica is suited to the separation of gases and the separation of water and other small molecule compounds from various organic compounds such as low molecular weight alcohols. In addition, compared to PDMS, hybrid silica has high heat resistance, and is suited to high temperature applications, for example, applications that involve concentration where accumulation is performed at low temperature before releasing at high temperature.

The separation membrane 51 is not limited to the above. The separation membrane may be a membrane that exhibits selective permeability for gases, includes membranes known as gas-diffusing porous membranes, membranes used in pervaporation, membranes used in penetrative vaporization, and the like, may be a polymer membrane, and may be a membrane with gas permeability, or a membrane capable of solubility diffusion. The separation membrane may be a membrane that is physically porous or may be a membrane that is porous on a molecular level, such as a polymer membrane with no holes or an inorganic membrane with fine pores on a molecular level.

With consideration to diffusivity and permeability, the thickness of such separation membrane 51 should be fpm to 1 mm, and more preferably around 50 μm to 500 μm, with the membrane strength also being extremely low due also to the composition. The strength of PDMS in particular is low. For this reason, in the exchange membrane unit 20, the separation membrane 51 is used having been reinforced by laminating a resin membrane 56 that is carbon fabric or the like with a thickness of around 50 to 500 μm having appropriate strength and high permeability, and a silk mesh 53 with a thickness of around 50 to 500 μm onto both surfaces of the separation membrane 51. It is also possible to reinforce only one surface of the separation membrane 51 in the manner described above. In addition, to prevent gaps from being produced between the separation membrane 51 and the housing 24, in the exchange membrane unit 20, the separation membrane 51 is tightly attached onto the housing 24 using an O ring 55.

The exchange membrane unit 20 additionally includes a first ionizing unit 71 that forms ions inside the first space 21 and a second ionizing unit 72 that forms ions inside the second space 22. The ionizing units 71 and 72 are typically plasma generating units that generate atmospheric-pressure plasma through corona discharge. Due to the corona discharge by the ionizing unit 71, the gas inside the first space 21, including the target substances that have passed through the separation membrane 51, is indirectly ionized. Accordingly, it is difficult for the target substances 29 to adhere to the inner walls of the housing 24 of the first space 21, which reduces the possibility of such target substances 29 acting as pollutants (contaminants).

From a cost perspective, dry air is suitable as the carrier gas 39 supplied to the first space 21, so that radicals such as ozone are generated by the corona discharge by the ionizing unit 71. Accordingly, the surfaces of the separation membrane 51 and the inner walls of the housing 24 that face the first space 21 are always activated by radicals such as ozone. This means that it is difficult for the target substances 29 and the like to adhere to the separation membrane 51 and the target substances 29 that appear at the surface of the separation membrane 51 are released into the first space 21 at early timing. In addition, since the chemical substances 29 that have passed through the separation membrane 51 and diffused into the first space 21 are ionized, it is also difficult for the chemical substances 29 to adhere to the part of the first exchange membrane unit 20 that forms the first space 21 and the first piping 25 that constructs the first path.

For this reason, there is very little adhesion of the target substances 29 that have passed through the separation membrane 51 to the surfaces of the membrane, the inner walls, and the like, so that the target substances 29 are carried by the carrier gas 39 in real time so as to be supplied to the ion mobility sensor 10. Since the target substances 29 do not act as pollutants and the target substances 29 are included in the carrier gas 39 without remaining in the exchange membrane unit 20, it is possible to improve the sensitivity and real time response of the ion mobility sensor 10.

The first ionizing unit 71 is not limited to a corona type and may be a direct ionizing unit using UV or the like. It is also possible to raise the sensitivity of the ion mobility sensor (FAIMS) 10 by disposing an indirect or direct ionizing unit of an appropriate type immediately before the ion mobility sensor 10 to promote ionization of the target substances 29.

In the same way as the ionizing unit 71 provided in the first space 21, the second ionizing unit 72 provided in the second space 22 activates the surfaces of the separation membrane 51 and the housing 24 that face the second space 22. Accordingly, it is possible to prevent the target substances 29 from accumulating in the second space 22 and to prevent, from the outset, such target substances 29 from subsequently passing through the separation membrane 51 and effectively becoming pollutants. Accordingly, it is possible to improve the precision of the measurement apparatus 1. The second ionizing unit 72 may be an atmospheric pressure plasma generation unit or may be another direct or indirect ionizing unit.

The exchange membrane unit 20 further includes thermoelectric elements 75 and 76 that indirectly heat and cool the separation membrane 51 and a temperature control unit 77 that controls such thermoelectric elements 75 and 76. The thermoelectric elements 75 and 76 may be provided so as to be dedicated to heating or cooling or may be used so as to be switched between heating and cooling by reversing the polarity of the supplied voltage. The temperature control unit 77 repeatedly heats and cools the separation membrane 51 with an appropriate cycle. Since the diffusion coefficient (permeability coefficient) falls when the separation membrane 51 is cooled, it becomes easy for the target substances 29 to accumulate on the separation membrane 51. Since the diffusion coefficient (permeability coefficient) rises when the separation membrane 51 is heated, the target substances 29 are discharged into the first space 21 including the target substances 29 accumulated on the separation membrane 51. Accordingly, it is possible to easily supply the target substances 29 in a concentrated state to the ion mobility sensor 10 via the carrier gas 39 and possible to improve the sensitivity of the measurement apparatus 1.

Figure 3:
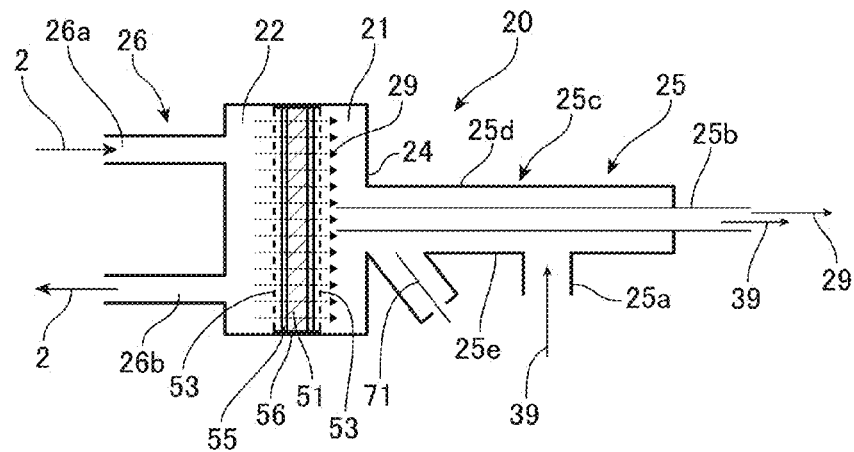
FIG. 3 is a block diagram showing an overview of another exchange membrane unit.

FIG. 3 shows an exchange membrane unit 20 of another type. For the exchange membrane unit 20 shown in FIG. 2, the sampled fluid 2 is a gas. On the other hand, for the exchange membrane unit (membrane unit of exchange) 20 shown in FIG. 3, by sampling a liquid, for example water, as the sample fluid 2 and passing the exchange membrane unit 20, it is possible to have gas and/or volatile components included in the water 2 pass through the separation membrane 51 into the first space 21. In this exchange membrane unit 20, if the separation membrane 51 functions as a pervaporation membrane, it is possible to selectively extract organic substances in a carrier gas from a mixture of organic liquids. Such exchange membrane unit 20 carries the target substances 29 that have passed through the separation membrane 51 to the ion mobility sensor 10 using the carrier gas 39, and is suited to applications that measure components included in a liquid such as water by carrying out analysis.

Figure 4:
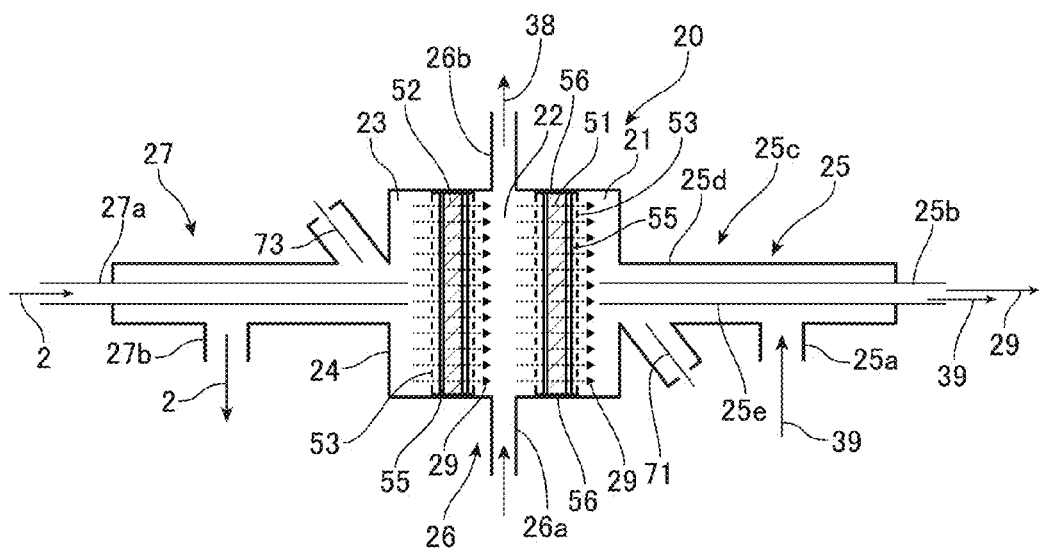
FIG. 4 is a block diagram showing an overview of yet another exchange membrane unit.

FIG. 4 shows the exchange membrane unit 20 of yet another type. Out of the components included in the sample fluid 2, one component for which removal by the exchange membrane unit 20 is desirable is water (steam, moisture). Although water becomes a reactant due to indirect ionization, which is useful when ionizing other components, when measurement is carried out at the ion mobility sensor 10, water appears as an extremely large peak (RIP) and is a factor that obstructs the detection and quantification of components that have peaks which overlap the RIP in the output (spectrum) of the ion mobility sensor 10.

The exchange membrane unit 20 shown in FIG. 4 includes a second separation membrane 52 in the housing 24 and the inside of the housing 24 is further divided by the second separation membrane 52 into the second space 22 and a third space (third room, third chamber) 23. Accordingly, the second space 22 is connected to the third space via the second separation membrane 52. The second separation membrane 52 is disposed substantially in parallel with the first separation membrane 51. In addition, the exchange membrane unit 20 further includes third piping system 27 that supplies and discharges a third fluid (sample fluid) 2 to and from the third space 23 and an ionizing unit 73 that is installed in the third space 23.

The third piping system 27 functions as a third path that supplies and discharges the sample fluid 2 to and from the third space 23. The third piping system 27 includes an input port 27a for the sample gas 2 and a discharge (output) port 27b for the sample gas 2, with the input port 27a being connected to the inlet port 3 of the measurement apparatus 1. The specific construction of the third piping system 27 is the same as the second piping system 26 of the exchange membrane unit 20 shown in FIG. 2.

A gas 38 composed of specified components, for example, air, nitrogen, and the like, that has been dried is supplied by the second piping system 26 to the second space 22 of the exchange membrane unit 20. One example of the gas 38 composed of specified components is a gas composed of components (molecules) of a type that is excluded by the first separation membrane 51 or a gas composed of components for which the ionization energy exceeds the ionization energy of the first ionizing unit 71. Since the components of a gas of this type are not ionized by the first ionizing unit 71, such components are not detected by the ion mobility sensor 10. Also, the second gas 38 composed of specified components may be a gas, such as air, for which the component composition and the ratio are known, and if components to be measured by the ion mobility sensor 10 are included, it will be possible to subsequently correct data.

In the exchange membrane unit 20, by having the sample gas 2 supplied to the third space 23 and the extracted components 29 pass the second separation membrane 52, the amount of water supplied to the ion mobility sensor 10 together with the target substances 29 falls. In addition, by supplying the dry air 38 to the second space 22 it is possible to reduce the moisture in the second space 22. This means that by passing the target substances 29 through the separation membrane 51, it is possible to greatly reduce the amount of water that appears in the first space 21 together with the target substances 29 and is carried by the carrier gas 39. Accordingly, at the ion mobility sensor 10, the RIP will become smaller and it will be possible to analyze chemical substances with peaks that overlap the RIP with even higher precision.

Figure 5:
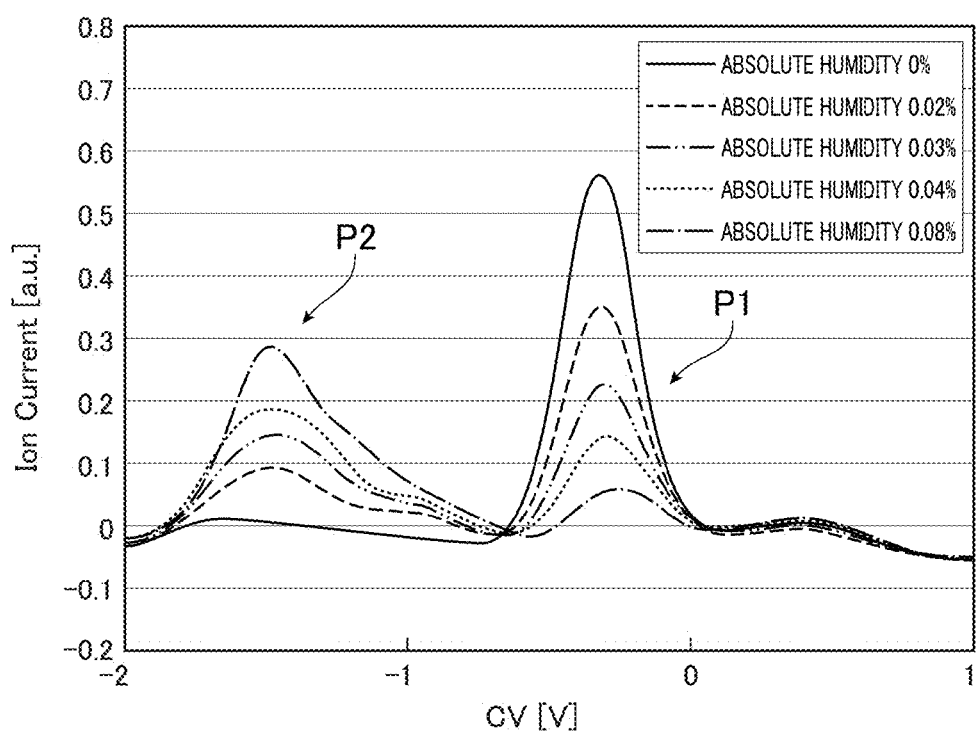
FIG. 5 is an example showing measurement results for sample gases with different humidity.

FIG. 5 shows an example where sample gas 2 including 700 ppb of acetaldehyde has passed the exchange membrane unit 20 and been measured by the FAIMS 10. The peak P1 in the drawing is the peak of acetaldehyde and the peak P2 is an RIP. As can be understood from this drawing, by removing water, the peak P1 of acetaldehyde becomes larger, which improves the detection sensitivity of the FAIMS 10.

Note that although a FAIMS is used as the ion mobility sensor 10 in the measurement apparatus 1 described above, the sensor may be another type of ion mobility sensor or a mass spectrometer. However, since it is possible for an ion mobility sensor to measure components (molecules) in air, this is favorable for a low-cost metal detecting system that is easy to manage. Also, although the measurement apparatus 1 has been described as an example in the preceding explanation, the system included in the present invention is not limited to a measurement apparatus and may be a monitoring apparatus that monitors a product line, breath monitoring that monitors components in breath, a mobile terminal with a function of determining health and/or determining risks by detecting chemical substances, or the like. One example of a system included in the present invention is a system that provides services, such as monitoring components like a gas with high humidity or a solution and providing content according to the result of monitoring.

The invention claimed is:

1. An exchange membrane unit comprising:
    a first separation membrane;
    a first space that is connected to a second space via the first separation membrane;
    a first path that supplies a first fluid to the first space and supplies chemical substances that have passed through the first separation membrane from the second space into the first space and diffused, to an ion detector using the first fluid discharged from the first space; and
    a first ionizing unit provided in the first space.

2. The exchange membrane unit according to claim 1,
    further comprising a second path that supplies and discharges a second fluid into and from the second space.

3. The exchange membrane unit according to claim 2,
    further comprising a second ionizing unit provided in the second space.

4. The exchange membrane unit according to claim 2,
    further comprising a second separation membrane that connects the second space and a third space,
    wherein the second fluid is a dried gas composed of specified components.

5. The exchange membrane unit according to claim 1, wherein the first ionizing unit includes a unit that generates atmospheric pressure plasma.

6. The exchange membrane unit according to claim 1, further comprising a thermoelectric conversion element that heats and cools the first separation membrane.

7. A system comprising:
the exchange membrane unit according to claim 1; and
the ion detector.

8. A system according to claim 7, wherein the ion detector is an ion mobility sensor.

\* \* \* \* \*